US011155531B2

(12) United States Patent
Yu et al.

(10) Patent No.: US 11,155,531 B2
(45) Date of Patent: Oct. 26, 2021

(54) N-LIPOIC-AMINO ACID OR PEPTIDE, DERIVATIVES AND THEIR USES

(71) Applicant: NEOSTRATA COMPANY, INC., Princeton, NJ (US)

(72) Inventors: Ruey J. Yu, Chalfont, PA (US); Eugene J. Vanscott, Abington, PA (US)

(73) Assignee: Neostrata Company, Inc., Princeton, NJ (US)

(*) Notice: Subject to any disclaimer, the term of this patent is extended or adjusted under 35 U.S.C. 154(b) by 102 days.

(21) Appl. No.: 16/083,924

(22) PCT Filed: Mar. 14, 2016

(86) PCT No.: PCT/US2016/022289
§ 371 (c)(1),
(2) Date: Sep. 11, 2018

(87) PCT Pub. No.: WO2017/160269
PCT Pub. Date: Sep. 21, 2017

(65) Prior Publication Data
US 2019/0161467 A1  May 30, 2019

(51) Int. Cl.
| | | |
|---|---|---|
| A61K 38/04 | (2006.01) |
| C07D 339/04 | (2006.01) |
| A61K 8/44 | (2006.01) |
| C07K 5/072 | (2006.01) |
| A61Q 19/02 | (2006.01) |
| A61K 47/64 | (2017.01) |
| C07K 5/078 | (2006.01) |
| A61K 45/06 | (2006.01) |
| A61K 8/49 | (2006.01) |
| A61K 8/64 | (2006.01) |
| A61K 9/00 | (2006.01) |
| A61Q 19/08 | (2006.01) |
| C07K 5/06 | (2006.01) |
| C07K 5/08 | (2006.01) |
| A61K 38/00 | (2006.01) |

(52) U.S. Cl.
CPC ............ *C07D 339/04* (2013.01); *A61K 8/44* (2013.01); *A61K 8/4986* (2013.01); *A61K 8/64* (2013.01); *A61K 9/0014* (2013.01); *A61K 45/06* (2013.01); *A61K 47/64* (2017.08); *A61Q 19/02* (2013.01); *A61Q 19/08* (2013.01); *C07K 5/06* (2013.01); *C07K 5/06121* (2013.01); *C07K 5/06165* (2013.01); *C07K 5/08* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,313,164 B1* | 11/2001 | Fujita | A61P 25/16 514/440 |
| 2002/0048798 A1 | 4/2002 | Avery et al. | |
| 2006/0216251 A1 | 9/2006 | Morariu | |
| 2007/0231284 A1 | 10/2007 | Pinel | |
| 2008/0200396 A1 | 8/2008 | Hocquaux | |
| 2010/0310484 A1* | 12/2010 | Hocquaux | A61Q 19/08 424/60 |
| 2011/0082192 A1 | 4/2011 | Milne | |
| 2011/0257130 A1 | 10/2011 | Rajagopal | |
| 2014/0303080 A1 | 10/2014 | Yu et al. | |
| 2015/0329519 A1 | 11/2015 | Kates et al. | |

FOREIGN PATENT DOCUMENTS

| | | | |
|---|---|---|---|
| CN | 1208035 A | | 2/1999 |
| EP | 1070710 A | | 1/2001 |
| JP | H 11-269170 A | | 10/1999 |
| JP | 00107071 | * | 1/2001 |
| JP | 2003 048833 A | | 2/2003 |
| JP | 2003286168 A | * | 10/2003 |
| JP | 2003286168 A | | 10/2003 |
| JP | 2006/022066 A1 | | 1/2006 |
| JP | 2016/000157 A | | 6/2014 |
| WO | WO 01/93824 A | | 12/2001 |
| WO | WO 2003/084532 A | | 10/2003 |
| WO | WO 2009/003284 A1 | | 1/2009 |
| WO | WO 2009/020317 A2 | | 2/2009 |

OTHER PUBLICATIONS

Ogata, JP 2003286168, English Translation furnished, 14 pages (Year: 2003).*
Gomes et al., "Alpha-lipoic acid as a pleiotropic compound with potential therapeutic use in diabetes and other chronic diseases", *Diabetology & Metabolic Syndrome* (2014) 6:80:1-18.
Kim et al., "Synthesis and anti-melanogenic effects of lipoic acid-polyethylene glycol ester", *Journal of Pharmacy and Pharmacology* (2008) 60:863-870.
Unno et al., "α-Lipoic Acid Melanogenesis in Three-dimensional Human Skin Model," Food Science Technology Research (2009) 15(5):537-540.
Wada et al., The Degradation and Regeneration of alpha-Lipoic Acid under the Irradiation of UV Light in the Existence of Homocysteine, *Journal Clin. Biochem. Nutr.* (May 2009) 44(3):218-222.

(Continued)

*Primary Examiner* — Satyanarayana R Gudibande
(74) *Attorney, Agent, or Firm* — Michelle Cristaldi (57) ABSTRACT

Novel compounds of N-Lipoic-amino acid, N-Lipoic-peptides and their derivatives are described. Also described are compositions and method of compositions containing the derivatives of the amino acids or peptides, and their uses including treating and preventing dermatological or cosmetic conditions or other disorders of the cutaneous system. Compositions and methods of using the compositions for skin lightening and cosmetics are also disclosed.

4 Claims, 6 Drawing Sheets

(56) References Cited

OTHER PUBLICATIONS

International search report and written opinion dated Sep. 2, 2016, for international application PCT/US2016/022289.
"Topical preparation useful as cosmetics for skin whitening and for 30 preventing or treating freckles, wrinkles and suntan, contains N-(alpha)-lipoyl amino acid or its salt", PN-JP2003286168 A20031007 DW200382, the abstract, published on Dec. 23, 2003.
Database WPI Week 200382. Thomson Scientific, London, GB; AN 2003-885517 XP002794570 & JP 2003286168 A (Senju Seiyaku KK) Oct. 7, 2003 *abstract*.
Lu Chichong et al: "Synthesis of lipoic acid-peptide conjugates and their effect on collagen and melanogene", European Journal of Medicinal Chemistry, Elsevier, Amsterdam, NL, vol. 69, Sep. 18, 2013 (Sep. 18, 2013), pp. 449-454, XP028762838, ISSN: 0223-5234, DOI: 1O.1O16/J.EJMECH.2O13.09.O11. *whole document*.
Yoshio VIII Deguchi et al: "Studies on the Synthesis of Thioctic Acid and its Related Compounds", Pharmaceutical Journal, vol. 83, No. 7, Jul. 25, 1963 (Jul. 25, 1963), pp. 733-737, XP55625496, DOI: 10.1248/yakushi1947.83.7_733. Compounds VII-XI.
Maria Laura Bolognesi et al: "Synthesis of New Lipoic Acid Conjugates and Evaluation of Their Free Radical Scavenging and Neuroprotective Activities", Chemical Biology & Drug Design, vol. 83, No. 6, Jun. 1, 2014 (Jun. 1, 2014), pp. 688-696, XP55625478, ISSN: 1747-0277, DOI: 10.1111/cbdd.12282. Compounds 5,6.
Koji Daigo et al: "Synthesis of some N-lipoyl amino acids and peptides", Journal of the American Chemical Society, vol. 84, No. 4, Feb. 1, 1962 (Feb. 1, 1962), pp. 662-665, XP55625481. Example compounds.
Di Stefano A et al: "L-dopa- and dopamine-(R)-alpha-lipoic acid conjugates as multifunctional codrugs with antioxidant properties", Journal of Medicinal Chemistry, American Chemical Society, US, vol. 49, No. 4, Feb. 23, 2006 (Feb. 23, 2006), pp. 1486-1493, XP002546289, ISSN: 0022-2623, DOI: 10.1021/JM051145P [retrieved on Jan. 26, 2006]. Compounds 1,2.
Steven A. Kates et al: "Lipoic acid analogs with enhanced pharmacological activity", Bioorganic & Medicinal Chemistry, vol. 22, No. 1, Jan. 2014 (Jan. 1, 2014), pp. 505-512, XP055118599, ISSN: 0968-0896, DOI: 10.1016/j.bmc.2013.10.057. Table 3.
Database WPI Week 200350. Thomson Scientific, London, GB; AN 2003-527674. XP002794571 & JP 2003 048833 A (Senju Seiyaku KK) Feb. 21, 2003 (Feb. 21, 2003) *abstract*.
Supplementary European Search Report for EP16894728 dated Sep. 25, 2019.

* cited by examiner

N-LIPOIC-AMINO ACID OR PEPTIDE, DERIVATIVES AND THEIR USES

CROSS-REFERENCE TO RELATED APPLICATIONS

This application is the national phase filing under 35 USC 371 of international application PCT/US2016/022289 filed on Mar. 14, 2016, the complete disclosure of which is hereby incorporated herein by reference for all purposes.

FIELD OF THE INVENTION

The embodiments described herein relate to compounds, compositions and uses of the compositions comprising N-Lipoic-amino acid or N-Lipoic-peptide, its derivative for topical administration to a subject to treat or prevent disorders, diseases, symptoms or syndromes associated with dermatological or cosmetic conditions or other disorders of the cutaneous system.

BACKGROUND OF THE INVENTION

Lipoic Acid, also known as alpha lipoic acid is one of the strongest antioxidant and has been widely used in skincare formulations, as a supplement and as a therapeutic compound. Lipoic acid is an essential co-factor for the mitochondrial energy metabolism. It reduces other water and fat soluble vitamins such as Vitamin C, E and glutathione and modulates glucose metabolism and inflammation. Lipoic Acid has been widely used and publicized in skin formulations as an anti-aging compound. However, lipoic acid has limited use due to its photosensitive nature and loss of biological activity.

Lipoic Acid is an essential cofactor for key enzymes in the mitochondrial oxidative pathway. It acts as a potent antioxidant and a metal chelator in the cellular environment (Gomes et al.). It has widely been used as an anti-oxidant for skin formulations. Lipoic acid has two optical enantiomers, R and S form of Lipoic Acid (Gomes et al.). Lipoic acid is used as an anti-aging compound in skin care products. However, since lipoic acid is photosensitive, it loses its biological effect when exposed to uv light (Wada et al.). Thus, more stable lipoic acid derivatives would be ideal for skin protection and anti-aging.

Certain studies demonstrate that lipoic acid has anti-melanogenic effects, where lipoic acid inhibits the expression of a key enzyme tyrosinase in the melanogenesis pathway (Kim J H et al.). Other studies demonstrate that lipoic acid derivatives scavenge DOPA quinone an intermediate in the melanin synthesis pathway. These studies demonstrate the lipoic acid derivatives inhibit melanin synthesis by more than one mechanism. However, since lipoic acid has only limited bioavailability in the skin due to its photosensitive nature, it is important to develop lipoic acid derivatives that are more stable.

Additionally, using high doses of lipoic acid is linked to certain adverse effects such as pruritus and skin ulcerations (Gomes et al.).

BRIEF SUMMARY OF THE INVENTION

The present invention relates to a compound which is a novel derivative of an amino acid or peptide comprising lipoic acid linked via a covalent amide bond to an amino acid or peptide. It has been discovered in the present invention that novel derivative of an amino acid or peptide, in particular N-Lipoic-amino acid or peptide and its derivative, and compositions for topical administration to a subject comprising a derivative of an amino acid or peptide according to the invention are therapeutically effective for treating or preventing disorders, diseases, symptoms or syndromes associated with dermatological or cosmetic conditions or other disorders of the cutaneous system.

In one general aspect, embodiments of the present invention relate to a compound which is a novel derivative of an amino acid or peptide having the following generic formula (I):

Formula (I)

or an isomer, free acid, base, salt, lactone, amide, hydroxylamide, hydrazide, ester, or nitrile thereof, wherein "N-Lipoic" is a lipoic (Lp) radical(s), attached to nitrogen atom of the amino or imino group in the amino acid radical $(X)_n$ is a peptide having n amino acid residues, each of the amino acid residue;

X is independently selected from any amino acid residue;

n is an integer from 0-2;

Z is a carboxyl-terminal amino acid residue;

each of the amino acid residue is independently selected from any amino acid;

$R_1$ is $OR_2$, $NHR_3$ and $NHNHR_4$;

$R_2$ is H, an alkyl, aralkyl or aryl radical having up to 9 carbon atoms;

$R_3$ or $R_4$ is independently H, OH, an alkyl, aralkyl, aryl or acyl radical having up to 9 carbon atoms.

In addition to the above, a side chain of each of the X and Z optionally and independently has an extra functional radical selected from the group consisting of OH, SH, $NHCONH_2$, $NHC(=NH)NH_2$, $NH_2$, COOH, $CONH_2$, imidazolyl, pyrrolidinyl, and indolyl;

the H of the extra functional radical is optionally substituted by $NH_2$, an acyl, alkyl, aralkyl, or aryl radical having up to 9 carbon atoms;

the H in $NH_2$, $NHNH_2$, NHOH, or $NH(C=NH)NH_2$ is optionally substituted by a lipoic radical.

A typical acyl radical includes, but is not limited to, acetyl (Ac), propanoyl (Pa), and benzoyl (Bz).

A typical group attached to the carboxyl-terminal amino acid residue includes, but is not limited to, OH, OEt, $NH_2$, NHOH, and $NHNH_2$, NHNHAc, NHNHPa or CN to replace carboxyl group.

In an embodiment, the derivative of lipoic amino acid is can be selected from the group consisting of: N-Lp-Gly-$NH_2$; N-Lp-Cys-$NH_2$; N-Lp-Tyr-$NH_2$; N-Lp-Tyr(OAc)-$NH_2$; N-Lp-Pro-$NH_2$; N-Lp-Cys-OH; N-Lp-Cys-OEt; N-Lp-Cys-(SAc)-OEt; and N-Lp-Cys-(SAc)-$NH_2$.

In another embodiment, the derivative of lipoic peptide is lipoic dipeptide may be selected from the group consisting of: N-Lp-Gly-Cys-$NH_2$; N-Lp-Pro-Cys-$NH_2$; N-Lp-Cys-Gly-$NH_2$; N-Lp-Tyr-Gly-$NH_2$; N-Lp-Gly-Tyr-$NH_2$; N-Lp-Tyr-Cys-$NH_2$; N-Lp-Tyr-Cys-OEt; N-Lp-Gly-Cys-OH; and N-Lp-Gly-Cys-OEt.

In another embodiment, the derivative of lipoic peptide is lipoic tripeptide selected from the group consisting of: N-Lp-Gly-Cys-Cys-$NH_2$; N-Lp-Cys-Cys-Cys-$NH_2$; N-Lp-Tyr-Cys-Cys-$NH_2$; N-Lp-Gly-Tyr-Cys-$NH_2$; and N-Lp-Pro-Cys-Cys-$NH_2$.

In a preferred embodiment, the derivative of lipoic amino acid is N-Lp-Gly-$NH_2$ which has the following structure Another aspect of the invention relates to a composition for topical administration to a subject, the composition comprising a therapeutically effective amount of the compound (comprising N-Lipoic-amino acid or N-Lipoic-peptide, or its derivative) as described with optionally a pharmaceutically or cosmetically acceptable carrier. The compound may be any lipoic amino acid, lipoic dipeptide, and lipoic tripeptide described in this disclosure. In a preferred embodiment, the lipoic amino acid is N-Lp-Gly-NH$_2$ preferably with a structure as defined above.

The invention also relates to a pharmaceutical composition for the topical treatment of skin changes associated with aging comprising an effective amount of a compound (comprising N-Lipoic-amino acid or N-Lipoic-peptide, or its derivative) as described above and optionally a pharmaceutically acceptable carrier adapted for topical delivery as a cosmetic product. The compound may be any lipoic amino acid, lipoic dipeptide, and lipoic tripeptide described in this disclosure. In a preferred embodiment, the lipoic amino acid is N-Lp-Gly-NH$_2$ preferably with a structure as defined above. In an embodiment, the composition comprises at least one compound which is not a derivative of N-Lipoic amino acid or a peptide; said compound selected from the group consisting of a sunscreen; an anti-acne compound; an anti-microbial compound; an anti-inflammatory compound; an antioxidant; a chelating compound; a pH adjuster; an emollient; a thickening compound; a preservative; an emulsifier; a humectant; a moisturizer; a suspending compound; an optical brightener; a stabilizer; a penetration enhancer; a perfume; and a coloring compound.

The invention also relates to a method of treating a cosmetic condition or dermatological disorder selected from the group consisting of disturbed keratinization, inflammation, and changes associated with intrinsic and extrinsic aging comprising topically administering to a subject a composition comprising therapeutically effective amount of a compound comprising N-Lipoic-amino acid or N-Lipoic-peptide, its derivative as described above.

In any of the embodiments, the cosmetic condition or dermatological disorder is selected from the group consisting of fine lines, wrinkles, age spots, and for skin lightening.

In another aspect, embodiments of the present invention relate to compositions for topical administration to a subject, the composition comprising a therapeutically effective amount of an amino acid or peptide derivative according to the invention, and optionally a pharmaceutically or cosmetically acceptable carrier.

In yet another aspect, embodiments of the present invention relate to methods of treating, preventing, alleviating or improving conditions, disorders, diseases, symptoms or syndromes associated with dermatological or cosmetic conditions or other disorders of the cutaneous system in a subject in need thereof, the method comprising topically administering to the subject a composition comprising a therapeutically effective amount of an amino acid or peptide derivative according to the present invention.

In yet another aspect, the present invention is directed to a skin lightening compound, the skin lightening additive comprising a novel derivative of an amino acid or peptide of this disclosure. In additional to skin lightening, novel derivative of an amino acid or peptide of this disclosure can also have an effect of inhibiting melanin and/or inducing procollagen.

In yet another aspect, the present invention is directed to a cosmetic composition for skin lightening, the cosmetic composition comprising a skin lightening compound as described above.

In another aspect, the present invention is directed to a method for lightening skin or treating aging related skin changes including fine lines and wrinkles with the cosmetic composition described above.

Cosmetic composition, as used herein, is meant to include a composition for topical application to skin of mammals, especially humans. Such a composition may be generally classified as leave-on or rinse off, and is meant to include conditioners or tonics, lipsticks, color cosmetics, and general topical compositions that in some fashion and at the very least, reduce the effect of melanin on keratinocytes. Lightening and whitening as used herein are meant to mean the same and they include the lightening of skin directly as well as the lightening of spots on the skin, like age spots and freckles.

The cosmetic composition of the present invention can be in the form of a liquid, lotion, cream, serum, gel, soap bar or toner, or applied via a face mask or patch. The composition of this invention is one that at the very least, lightens skin when skin is meant to include skin on the face, neck, chest, back, arms, hands, legs and scalp.

Another embodiment relates to a therapeutic composition comprising a compound (comprising N-Lipoic-amino acid or N-Lipoic-peptide, or its derivative) for the treatment of a dermatological disorder. Another embodiment relates to the use of a compound (comprising N-Lipoic-amino acid or N-Lipoic-peptide, or its derivative) in the manufacture of a medicament in the treatment of a dermatological disorder.

In another embodiment, the present invention provides the use of a compound according to the present invention in the manufacture of a medicament for treating a dermatological disorder. In a further aspect the present invention also provides a method for manufacturing a medicament comprising a composition according to the present invention. Preferably the method of the invention includes a step which sterilizes the medicament. The dermatological disorder may be any disorder discussed in this disclosure.

DESCRIPTION OF THE INVENTION

An amino acid is an organic acid having one or more than one alkaline radical such as amino, guanidino, imino, or hydrazine radical attached at any carbon atom other than carbon one. There are 20 common amino acids which are represented by chemical names, such as "glycine", or abbreviated symbols such as three letters, "Gly" or one letter "G. In this disclosure, both one letter and three letters will be used. Except glycine, all other common amino acids have stereoisomers, i.e., enantiomer, D or L form. The amino acids in most natural peptides and proteins are all in L-form. Some D-form amino acids are produced by microorganisms or present in antibiotics, and have inhibitory or antagonistic actions. For example, D-alanine, D-aspartic acid, and D-glutamic acid are present in bacterial cell walls, and D-glutamic acid, D-aspartic acid and D-phenylalanine are present in the antibiotic bacitracin. An uncommon amino acid is an amino acid that is not a common amino acid. Examples of uncommon amino acids include, but are not limited to, β-alanine and taurine. The uncommon amino acids can exist as a D or L form.

The one letter and three letter symbols used for the 20 common amino acids are as follows: alanine (A, Ala), arginine (R, Arg), aspartic acid (D, Asp), asparagine (N, Asn), cysteine (C, Cys), glycine (G, Gly), glutamic acid (E, Glu), glutamine (Q, Gln), histidine (H, His), isoleucine (I, Ile), leucine (L, Leu), lysine (K, Lys), methionine (M, Met), phenylalanine (F, Phe), proline (P, Pro), serine (S, Ser), threonine (T, Thr), tryptophan (W, Trp), tyrosine (Y, Tyr) and valine (V, Val).

The letter symbols used for uncommon amino acids are as follows: β-alanine (bAla), 4-aminobenzoic acid (Aba), 2-aminobutanoic acid (Abu), 4-aminobutanoic acid (4Abu), 2-aminoisobutanoic acid (Aib), 5-aminolevulinic acid (All), alliin (Ali), 2-aminoadipic acid (Aad), 3-aminoadipic acid (bAad), aminopimelic acid (Apa); 3-aminotyrosine (Atyr), canavanine (Cav), canaline (Can), ciliatine (Cil), cysteic acid (Cya), cysteine sulfinic acid (Csa), citruline (Cit); creatine (Cre), creatinine (Cm); 2,3-diaminosuccinic acid (Dsa); 2,4-diaminobutanoic acid (Dbu); 2,3-diaminopropanoic acid (Dpr); 3,4-dihydroxyphenyl-alanine (Dopa); 3,5-diiodotyrosine (Dtyr); homoarginine (Har), homoserine (Hser), homocysteine (Hcys), homocitrulline (Hcit), hydroxylysine (Hyl); 3-hydroxyproline (3Hyp); 4-hydroxyproline (4Hyp); 2-hydroxy-4-aminobutanoic acid (Haba); 3-hydroxy-4-aminobutanoic acid (Hyba); 4-hydroxyornithine (Horn); 4-hydroxyaspartic acid (Hasp); 4-hydroxyphenyl-glycine (Hpg); 3-iodotyrosine (Ityr), lanthionine (Lan), β-lysine (βLys); α-methylalanine (Mala); β-methylaspartic acid (Mas), 4-methylproline (Mpro); 2-methylserine (Mser); N-methylhistidine (Mhis); ornithine (Orn); phenylglycine (Pgly); 3-phenylserine (Pser); sarcosine (Sar); S-allyl-cysteine (Sac); theanine (The); thyroxine (Thy); 3,5,3'-triiodothyronine (Tth); and taurine (Tau).

The terms and abbreviations used in this application are as follows: lipoic, Lp; formyl, Fo; acetyl, Ac; propanoyl, Pa; benzoyl, Bz; pyroglutamyl, Pyro; phenylacetyl, PhAc; benzyloxycarbonyl, Z; methyl ester, OMe; ethyl ester, OEt; propyl ester, OPr; butyl ester, OBu; t-butyl ester, OtBu; hexyl ester, OHex; octyl ester, OOc; benzyl ester, Obzl.

A peptide with amide covalent bonds is formed from at least two amino acids when the carboxyl group of one amino acid reacts with the amino group of the other amino acid in a dehydration synthesis reaction. A dipeptide is a peptide that contains two amino acid residues. A tripeptide is a peptide that contains three amino acid residues. Peptides can be further modified by substitutions or derivations. Each peptide can have different chemical and physical properties, and has different biological and pharmacological actions.

As used herein, a "derivative" of a compound is defined as a compound molecule formed by substitution of one or more functional groups in the compound. Examples of which include acylation of OH, $NH_2$, $NHNH_2$, NHOH, and NH(C=NH)$NH_2$, esterification of COOH, change from COOH to an amide, hydroxylamide, hydrazide or nitrile, or substitution of H in $NH_2$, $NHNH_2$, NHOH, or NH(C=NH)$NH_2$, or by a lipoic radical.

In one general aspect, embodiments of the present invention relate to a compound which is a novel derivative of an amino acid or peptide having the following generic formula (I):

N-Lipoic-$(X)_n$-Z-$R_1$            Formula (I)

or an isomer, free acid, base, salt, lactone, amide, hydroxylamide, hydrazide, ester, or nitrile thereof, wherein "N-Lipoic" is a lipoic (Lp) radical(s); attached to nitrogen atom of the amino or imino group in the amino acid radical, $(X)_n$ is a peptide having n amino acid residues, each of the amino acid residue X is independently selected from any amino acid residue;

n is an integer from 0-2;

Z is a carboxyl-terminal amino acid residue, each of the amino acid residue is independently selected from any amino acid;

$R_2$ is $OR_2$, $NHR_3$ or $NHNHR_4$;

$R_2$ is H, an alkyl, aralkyl or aryl radical having up to 9 carbon atoms;

$R_3$ or $R_4$ is independently H, OH, an alkyl, aralkyl, aryl or acyl radical having up to 9 carbon atoms;

a side chain of each of the X and Z optionally and independently has an extra functional radical selected from the group consisting of OH, SH, $NHCONH_2$, NHC(=NH)$NH_2$, $NH_2$, COOH, $CONH_2$, imidazolyl, pyrrolidinyl, and indolyl;

the H of the extra functional radical is optionally substituted by $NH_2$, an acyl, alkyl, aralkyl, or aryl radical having up to 9 carbon atoms;

the H in $NH_2$, $NHNH_2$, NHOH, or NH(C=NH)$NH_2$ is optionally substituted by a lipoic radical.

A typical acyl radical includes, but is not limited to, acetyl (Ac), propanoyl (Pa), and benzoyl (Bz).

A typical group attached to the carboxyl-terminal amino acid residue includes, but is not limited to, OH, OEt, $NH_2$, NHOH, and $NHNH_2$, NHNHAc, NHNHPa or CN to replace carboxyl group.

In another aspect, embodiments of the present invention relate to compositions for topical administration to a subject, the composition comprising a therapeutically effective amount of an amino acid or peptide derivative according to the invention, and optionally a pharmaceutically or cosmetically acceptable carrier.

According to another embodiment of the present invention, a derivative of an amino acid or a peptide can also be a di(Lipoic) residue, wherein an additional Lipoic residue is attached to an extra functional group of X or Z in formula (I), and preferably to an amino group via a covalent amide bond.

Representative N-Lipoic-amino acids or peptides, their derivatives according to the invention include, but are not limited to (1) N-Lp-$(X)_n$-Z-$R_1$.

(1) N-Lipoic-amino acid or peptide derivatives: N-Lp-$(X)_n$-Z-$R_1$

Representative N-Lipoic-amino acid derivatives include, but are not limited to the following:

N-Lp-Z-$R_1$, wherein Z is selected from any amino acid including A; R; D; N; C; G; E; Q; H; I; L; K; M; F; P; S; T; W; Y; V; bAla; Aba; Abu; 4Abu; Aib; All; Ali; Aad; bAad; Apa; Atyr; Cav; Can; Cil; Cya; Csa; Cit; Cre; Cm; Dsa; Dbu; Dpr; Dopa; Dtyr; Har; Hser; Hcys; Hcit; Hyl; 3Hyp; 4Hyp; Haba; Hyba; Horn; Hasp; Hpg; Ityr; Lan; βLys; Mala; Mas; Mpro; Mser; Mhis; Orn; Pgly; Pser; Sar; Sac; The; Thy; Tth; Tau.

The amino acid Z can be an isomer, free acid, base, salt, lactone, amide, hydroxylamide, hydrazide, ester or nitrile form, such as OH, $NH_2$, NHOH, $NHNH_2$, NHNHAc, NHNHPa, OEt, OPr and CN form.

The preferred lipoic amino acid derivatives are as following: N-Lp-Gly-$NH_2$; N-Lp-Cys-$NH_2$; N-Lp-Tyr-$NH_2$; N-Lp-Tyr(OAc)-$NH_2$; N-Lp-Pro-$NH_2$; N-Lp-Cys-OH; N-Lp-Cys-OEt; N-Lp-Cys-(SAc)-OEt; and N-Lp-Cys-(SAc)-$NH_2$.

The preferred lipoic dipeptide derivatives are as following: N-Lp-Gly-Cys-$NH_2$; N-Lp-Pro-Cys-$NH_2$; N-Lp-Cys-Gly-$NH_2$; N-Lp-Tyr-Gly-$NH_2$; N-Lp-Gly-Tyr-$NH_2$; N-Lp-Tyr-Cys-$NH_2$; N-Lp-Tyr-Cys-OEt; N-Lp-Gly-Cys-OH; and N-Lp-Gly-Cys-OEt.

The preferred lipoic tripeptides derivatives are as following: N-Lp-Gly-Cys-Cys-$NH_2$; N-Lp-Cys-Cys-Cys-$NH_2$; N-Lp-Tyr-Cys-Cys-$NH_2$; N-Lp-Gly-Tyr-Cys-$NH_2$; and N-Lp-Pro-Cys-Cys-$NH_2$ N-Lipoic-amino acid or peptide and its derivative according to embodiments of the present invention can be made by any method known to those skilled in the art in view of the present disclosure.

Another general aspect of the present invention relates to a method of treating, preventing, alleviating or improving conditions, disorders, diseases, symptoms or syndromes associated with dermatological or cosmetic conditions or other disorders of the cutaneous system. The method comprises topically administering to the subject a composition comprising a therapeutically effective amount of a derivative of an amino acid or a peptide according to the invention, and optionally a pharmaceutically or cosmetically acceptable carrier.

Conditions, disorders, symptoms and syndromes associated with the cutaneous system that can be treated with a composition of the present invention are described as follows.

Cutaneous System

The cosmetic, dermatological or other conditions and disorders of cutaneous system that can be treated with a composition of the present invention include, but are not limited to, infections, deranged or disordered cutaneous or mucocutaneous tissue relevant to skin, nail and hair; oral, vaginal and anal mucosa; disturbed keratinization; inflammation; changes associated with intrinsic and extrinsic aging. The manifestations include, but are not limited to, oily skin; acne; rosacea; age spots; blemished skin; blotches; cellulite; dermatoses; dermatitis; skin, nail and hair infections; dandruff; dryness or looseness of skin, nail and hair; xerosis; inflammation, or eczema; elastosis; herpes; hyperkeratosis; hyperpigmented skin; ichthyosis; keratoses; lentigines; melasmas; mottled skin; pseudofolliculitis barbae; photoaging and photodamage; pruritus; psoriasis; skin lines; stretch marks; thinning of skin, nail plate and hair; warts; wrinkles; oral or gum disease; irritated, inflamed, red, unhealthy, damaged or abnormal mucosa, skin, hair, nail, nostril, ear canal, anal or vaginal conditions; breakdown, defective synthesis or repair of dermal components; abnormal or diminished synthesis of collagen, glycosaminoglycans, proteoglycans and elastin, as well as diminished levels of such components in the dermis; uneven skin tone; uneven and rough surface of skin, nail and hair; loss or reduction of skin, nail and hair resiliency, elasticity and recoilability; laxity; lack of skin, nail and hair lubricants and luster; fragility and splitting of nail and hair; yellowing skin; reactive, irritating or telangiectatic skin; and dull and older-looking skin, nail and hair. In addition, the composition of the current invention can be used for general care of skin, nail and hair; to improve skin texture and pores, flakiness and redness; to make skin soft, smooth, fresh, balanced, visibly clear, even-toned and brighter; to increase skin fullness and plumpness; and for skin bleach and lightening and wound healing; to reduce or prevent sweating or perspiration of underarm, crotch, palm, or other parts of the body.

Skin, nail and hair infections can be caused by microorganisms which include bacteria, fungi, yeasts, molds, parasites and viruses. More specifically, the bacterial infections can cause trichomycosis axillaris, pitted keratolysis, erythrasma, impetigo, ecthyma, furunculosis (boils), carbuncle, scalded skin syndrome, toxic shock syndrome, erysipelas, cellulitis, necrotizing fasciitis, erysipeloid, cat-scratch disease (*Rochalimaea henselae*), syphilis, lyme disease (*Borrelia burgdorferi*), cutaneous anthrax (*Bacillus anthracis*), gonococcal septicaemia, inoculation tuberculosis, scrofuloderma, tuberculides, erythema induratum, leprosy (*Mycobacterium leprae*), leishmaniasis and acute paronychia. The viral infections can cause viral warts (human papilloma virus), varicella (chickenpox), herpes zoster (varicella-zoster), herpes simplex (herpesvirus hominis), molluscum contagiosum, orf, AIDS (acquired immunodeficiency syndrome, human immunodeficiency virus, HIV), herpangina, mucocutaneous lymph node syndrome (Kawasaki's disease), Gianotti-Crosti syndrome (hepatitis B virus), measles, rubella and erythema infectiosum. The fungal infections can cause ringworm, tinea pedis (athlete's foot), tinea unguis (nail infection), tinea hands, tinea groin, tinea trunk and limbs, tinea capitis (scalp), oral candidiasis, candida intertrigo, genital candidiasis, chronic paronychia, chronic mucocutaneous candidiasis, pityriasis versicolor, histoplasmosis, coccidioidomycosis, blastomycosis, sporotrichosis, actinomycosis and mycetoma (madura foot). The antibiotic resistant microorganisms include methicillin-resistant *Staphyloccocus aureus* (MRSA), and *Staphyloccocus epidermidis* (MRSE).

Administration Routes and General Preparations

Compositions comprising a derivative of an amino acid or a peptide according to the invention, such as N-Lipoic-amino acid or peptide or its derivative, can be administered to a subject in need by topical applications known to those skilled in the art.

For topical application, the composition comprising a derivative of an amino acid or a peptide of the present invention can be formulated as a solution, gel, lotion, cream, oil-in water emulsion, water-in-oil emulsion, ointment, shampoo, spray, stick, powder, mask, pads, mouth rinse or wash, vaginal gel or suppositories, rectal gel or suppositories, urethral gel or suppositories or other form acceptable for use on skin, nail, hair, oral mucosa, vaginal or anal mucosa, mouth or gums. The concentration of the derivative of an amino acid or a peptide can be about 0.001% to about 99% by weight or volume of the total composition.

In another embodiment, the composition may further comprise an additional cosmetic, pharmaceutical, or other compound to achieve synergetic or synergistic effects in the treatment or prevention of diseases, disorders, and syndromes associated with dermatological or cosmetic conditions or other disorders of the cutaneous system. To prepare a topical combination composition, a cosmetic, pharmaceutical or other compound is incorporated into any one of the above compositions by dissolving or mixing the compound into the formulation. Other forms of compositions for topical delivery of N-Lipoic-amino acid or peptide or its derivative of the present invention are readily recognized by those skilled in the art.

Cosmetics

In another aspect, embodiments of the present invention relate to a novel derivative of N-Lipoic amino acid or peptide, serving as an anti-aging and/or skin lightening compound in a cosmetic composition. The cosmetic compositions of the present invention typically comprise from about 0.001% to about 99% by weight, and preferably, from about 0.01% to about 20%, and most preferably, from about 0.1% to about 10% by weight of the novel derivative of N-Lipoic amino acid or peptide, based on total weight of the cosmetic composition and including all ranges subsumed therein. Other preferred ranges include about 0.001% to 0.05%; about 0.001% to 0.5%; about 0.001% to 1%; and about 0.001% to 2%.

The packaging for the composition of his invention can be a patch, bottle, tube, roll-ball applicator, propellant driven aerosol device, squeeze container or lidded jar.

In any compositions of the invention, the composition may comprise at least one compound which is not a derivative of N-Lipoic amino acid or a peptide. This compound may be, for example, one or more selected from a sunscreen; an anti-acne compound; an anti-microbial compound; an anti-inflammatory compound; an antioxidant; a chelating compound; a pH adjuster; an emollient; a thickening compound; a preservative; an emulsifier; a humectant; a moisturizer; a suspending compound; an optical brightener; a stabilizer; a penetration enhancer; a perfume; and a coloring compound.

Lipoic Acid Derivatives

In a preferred embodiment, the novel derivative of N-Lipoic amino acid or peptide is a derivative of Lipoic Acid.

We developed various lipoic acid derivatives with enhanced stability and anti-melanogenic effects. Among the derivative N-lipoic glycinamde (L20) demonstrated significant melanin reduction in normal human epidermal melanocytes and MelanoDerm models. The structure of L20 is as follows:

At non-toxic does L20 completely blocked melanin synthesis, where the melanocytes did not have any measureable melanin. The effect of L20 was tested using 3-dimensional skin co-culture MelanoDerm models. L20 inhibited melanin synthesis in 24 h observed by microscopic evaluation. At non-toxic doses L20 reduced melanin content of keratinocyte-melanocyte co-cultures by 56% in darkly pigmented skin biopsies. Additionally, one week regression study resulted in reversible inhibition of melanin synthesis. Using normal dermal skin equivalents (EpiDerm-FT) L20 induced pro-collagen in the fibroblast-keratinocyte co-cultures. Thus, L20 is a promising compound for skin hyperpigmentation and anti-aging effects including fine lines and wrinkles.

We synthesized various lipoic acid derivatives, these include, N-lipoic glycinamide, and N-Lipoic cysteinamide These lipoic acid derivatives are more stable than lipoic acid. Therefore, it is essential to use non-toxic doses for skin care products.

In this disclosure we synthesis various novel derivative of N-Lipoic amino acid or peptide which are Lipoic Acid derivatives and tested them for their ability as an anti-melanogenic, anti-aging and anti-oxidant properties.

The preferred lipoic amino acid derivatives are as following: N-Lp-Gly-NH$_2$; N-Lp-Cys-NH$_2$; N-Lp-Tyr-NH$_2$; N-Lp-Tyr(OAc)-NH$_2$; N-Lp-Pro-NH$_2$; N-Lp-Cys-OH; N-Lp-Cys-OEt; N-Lp-Cys-(SAc)-OEt; and N-Lp-Cys-(SAc)-NH$_2$.

The preferred lipoic dipeptide derivatives are as following: N-Lp-Gly-Cys-NH$_2$; N-Lp-Pro-Cys-NH$_2$; N-Lp-Cys-Gly-NH$_2$; N-Lp-Tyr-Gly-NH$_2$; N-Lp-Gly-Tyr-NH$_2$; N-Lp-Tyr-Cys-NH$_2$; N-Lp-Tyr-Cys-OEt; N-Lp-Gly-Cys-OH; and N-Lp-Gly-Cys-OEt.

The preferred lipoic tripeptides derivatives are as following:
N-Lp-Gly-Cys-Cys-NH$_2$; N-Lp-Cys-Cys-Cys-NH$_2$; N-Lp-Tyr-Cys-Cys-NH$_2$; N-Lp-Gly-Tyr-Cys-NH$_2$; and N-Lp-Pro-Cys-Cys-NH$_2$.

The following examples are to further illustrate the nature of the invention. It should be understood that the following examples do not limit the invention, and that the scope of the invention is determined by the appended claims.

EXAMPLES

Example 1: Measurement of Skin Thickness Using Micrometer Calipers

In a study related to skin changes associated with aging, skin thickness was measured by micrometer calipers as follows.

The skin was grasped with a 2×6 cm metal hinge; the internal faces of which were coated with emery cloth to prevent slippage, and manually squeezed to threshold subject discomfort. Combined thickness of two whole-skin layers including thickness of the two hinge leaves was measured with micrometer calipers. Thickness of the two hinge leaves was subtracted to determine the actual thickness of two whole-skin layers. Triplicate measurements on sites treated with a composition of the present invention were done and an average number was used for calculation of the skin thickness.

Example 2: Measurement of Skin Thickness Using an Electronic Digital Caliper In a study related to skin changes associated with aging, skin thickness was measured by an electronic digital caliper as follows.

Test sites of skin 17 mm in diameter were used, the circular sites were marked with permanent ink. Intervening control sites were also 17 mm in diameter. Test sites were treated with a composition of the present invention at the test sites and a control at the control sites. Thickness of skin of all sites was measured directly by means of an electronic digital caliper. In this instance the jaws of the caliper were opened to 17 mm, applied with pressure to the skin sites and then closed to firm tightness. Thickness of skin was then read off the screen of the calipers. Measurements of all sites were made in triplicate.

Example 3: Formulations

A typical aqueous solution composition comprising an N-Lipoic-amino acid or peptide compound, or its derivative according to the present invention is formulated as follows. All the amino acids or the peptides except glycine were in L-form.

An N-Lipoic-amino acid or peptide compound, or its derivative according to the present invention, 0.1-1.0 g, was dissolved in 99.9-99.0 ml solution prepared from 40 parts water, 40 parts ethanol and 20 parts propylene glycol by volume (hereinafter referred to as WEP442), or 80 parts ethanol and 20 parts propylene glycol by volume (hereinafter referred to as EP82), The solution thus formulated contained 0.1%-1% (w/v) N-Lipoic-amino acid or peptide compound or its derivative of the present invention in solution composition. Under similar conditions, solution compositions containing different concentrations of N-Lipoic-amino acid or peptide compound or its derivative of the present invention were readily formulated.

The solution or other compositions thus prepared or formulated are believed to be therapeutically effective for treatment of various medical disorders including nervous, vascular, muscular-skeletal or cutaneous systems. Also, these solutions and compositions are believed to be therapeutically effective for treatment of inflammatory diseases including eczema, psoriasis and aging-related skin changes including age spots, wrinkles etc.

Example 4: Formulations

As an illustration, N-Lp-O—Ac—Y—$NH_2$ 0.2 g was dissolved in 99.8 ml EP82. The solution composition thus formulated with pH 6.7 contained 0.2% (w/v) N-Lp-O—Ac—Y—$NH_2$. Under similar conditions, N-Lp-Y—$NH_2$ 0.2 g was dissolved in 99.8 ml EP82. The solution composition thus formulated with pH 6.7 contained 0.2% (w/v) N-Lp-Y—$NH_2$.

Under similar conditions, N-Lp-P—$NH_2$ 0.1 g was dissolved in 99.9 ml EP82. The solution composition thus formulated with pH 6.8 contained 0.1% (w/v) N-Lp-P—$NH_2$.

Under similar conditions, N-Lp-G-$NH_2$ 0.2 g was dissolved in 99.8 ml WEP442. The solution composition thus formulated with pH 5.9 contained 0.2% (w/v) N-Lp-G-$NH_2$.

Under similar conditions, N-Lp-G-$NH_2$ 0.4 g was dissolved in 99.6 ml WEP442. The solution composition thus formulated with pH 5.6 contained 0.4% (w/v) N-Lp-G-$NH_2$.

The solution compositions or other formulations are believed to be therapeutically effective for treatment of acne and aging-related skin changes including wrinkles, age spots and for skin lightening.

Example 5

A typical anhydrous composition in solution form containing N-Lypoic amino acid or peptide was formulated as follows:

N-Lp-Tyr-$NH_2$ 200 mg was dissolved in 100 ml solution prepared from 30 parts Propylene Glycol, 40 parts Ethanol, and 30 parts Oleyl Lactate by volume (hereinafter referred to as PAO343). The composition thus formulated contained 0.2% N-Lp-Tyr-$NH_2$ in PAO343.

Under the same conditions in (A) the following N-Lypoic amino acid derivatives in anhydrous composition were formulated.

N-Lp-Tyr(OAc)-$NH_2$ 0.2% in PAO343.
N-Lp-Pro-$NH_2$ 0.2% in PAO343.
N-Lp-Gly-$NH_2$ 0.2% in PAO343.
Lp-Cys-OEt 0.2% in PAO343.

Example 6

Another anhydrous composition in solution form containing N-Lypoic amino acid or peptide was formulated as follows:

N-Lp-Tyr-$NH_2$ 200 mg was dissolved in 100 ml solution prepared from 30 parts Propylene Glycol and 70 parts Ethanol by volume (hereinafter referred to as EP73).

The composition thus formulated contained 0.2% N-Lp-Tyr-$NH_2$ in EP73.

Under the same conditions in (B) the following N-Lypoic amino acid derivatives in anhydrous composition were formulated.

Lp-Cys-OEt 0.2% in EP73.
Lp-Cys-OH 0.2% in EP73.

Example 7

Another anhydrous composition in cream form containing N-Lypoic amino acid or peptide was formulated as follows:

N-Lp-Pro-$NH_2$ 200 mg was dissolved in 20 ml Propylene Glycol and the solution thus prepared was mixed with 80 g melted mixture prepared from 20 parts Propylene Glycol, 30 parts Oleyl Lactate, 5 parts beeswax, 5 parts glyceryl monostearate, 5 parts PEG-40 stearate, 35 parts shea butter by weight.

The composition thus formulated in cream form contained 0.2% N-Lp-Pro-$NH_2$ in anhydrous cream.

Under the same conditions a composition containing Lp-Cys-OEt 0.2% in anhydrous cream was readily formulated.

The above compositions as formulated in Examples 4-7 are believed to be therapeutically effective for skin lightening and topical treatments of inflammatory disorders and age-related skin changes including Eczema, psoriasis, age spots, fine lines, wrinkles, etc.

Example 8: Formulations

The solution compositions or other formulations are believed to be therapeutically effective for treatment of inflammatory diseases including eczema, psoriasis, acne and aging-related skin changes including wrinkles, age spots and for skin lightening.

Example 9: L20 Inhibits Melanin and Induces Procollagen

Figure 1A:
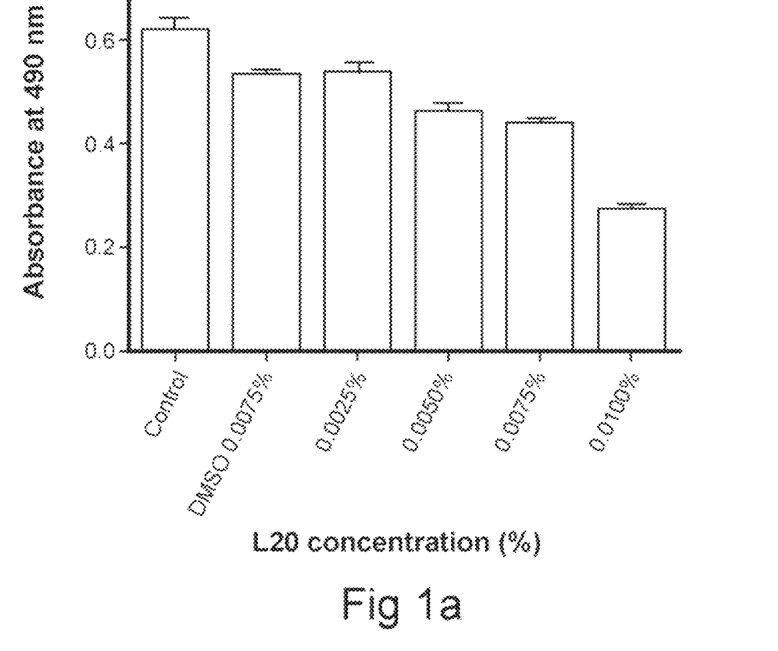
FIG. 1 depicts N-Lp-Gly-NH$_2$ (L20) significantly blocks melanin synthesis of normal neonatal human epidermal melanocytes.
Figure 1B:
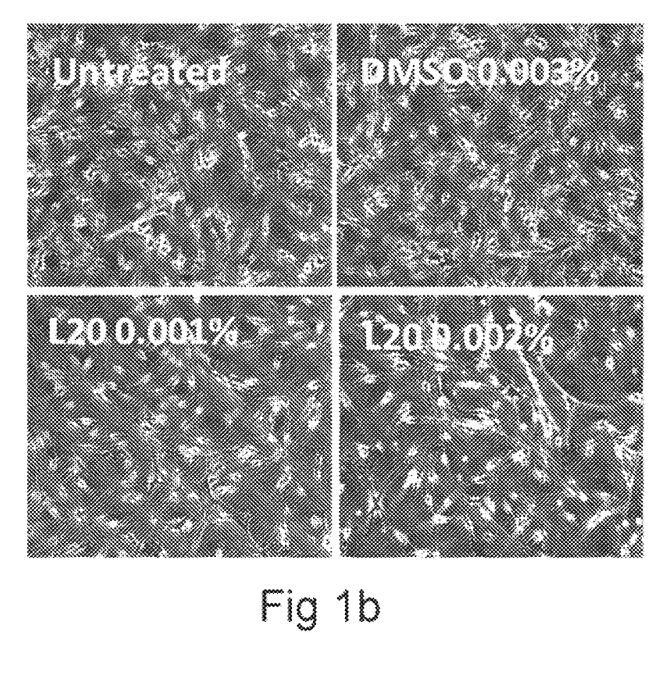
Figure 1C:
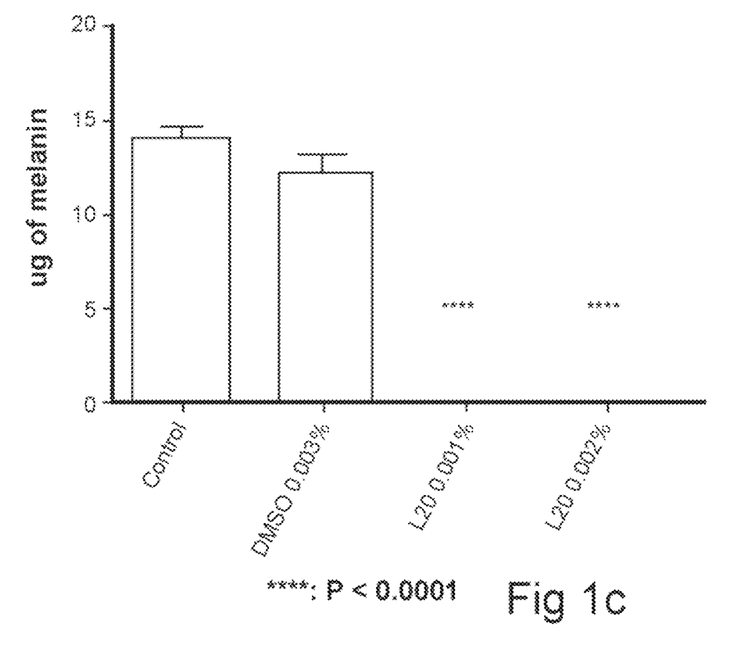

L20 Inhibits Melanin Synthesis in Normal Neontal Human Epidermal Melanocytes to Undetectable Levels L20 is a glycinamide derivative of lipoic acid and was treated on normal human epidermal melanocytes at different doses for 48 h. Doses more than 0.05% L20 appeared to have moderate toxicity (FIG. 1a). We determined the ability of L20 to inhibit melanin synthesis in melanocyte cultures. L20 was used at a non-toxic dose of 0.001% for 7 days (FIG. 1b), their treatment was carried on consecutive days. After a week of treatment, the melanin was extracted and quantified using a melanin standard curve. L20 treated normal melanocytes had no detectable melanin compared to untreated control and DMSO treated control (FIG. 1c).

Figure 2A:
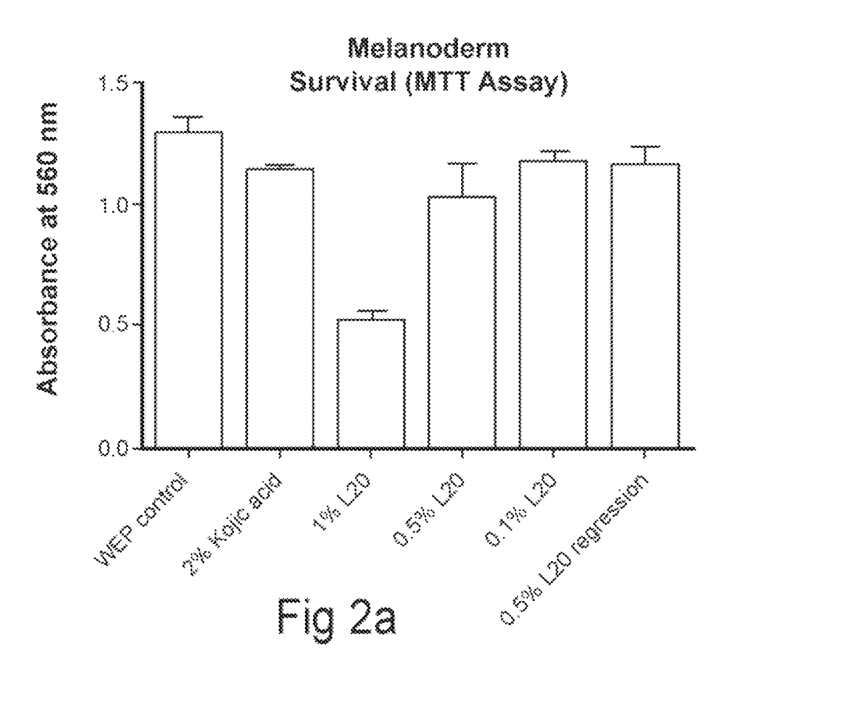
FIG. 2 depicts L20 significantly blocks melanin synthesis of normal adult human Melanoderm 3D co-cultures.
Figure 2B:
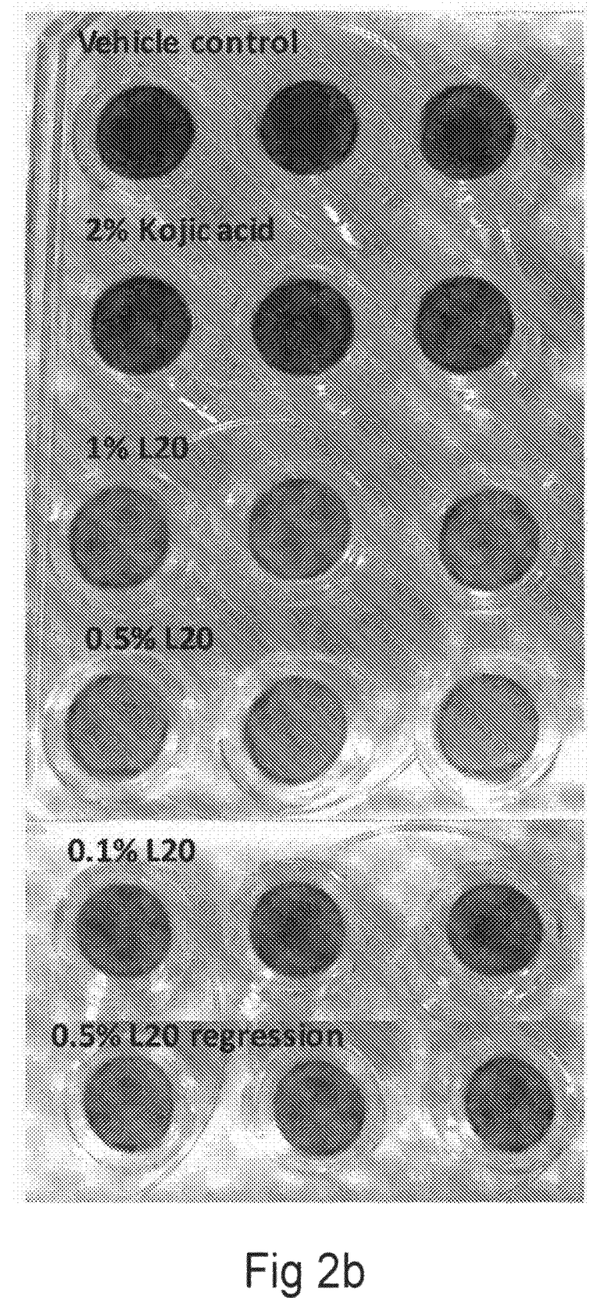
Figure 2C:
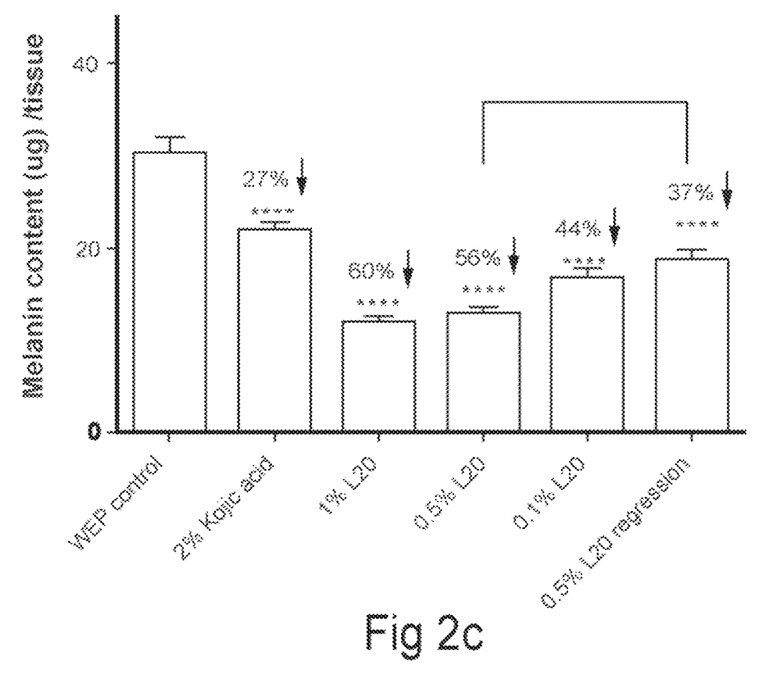
Figure 2D:
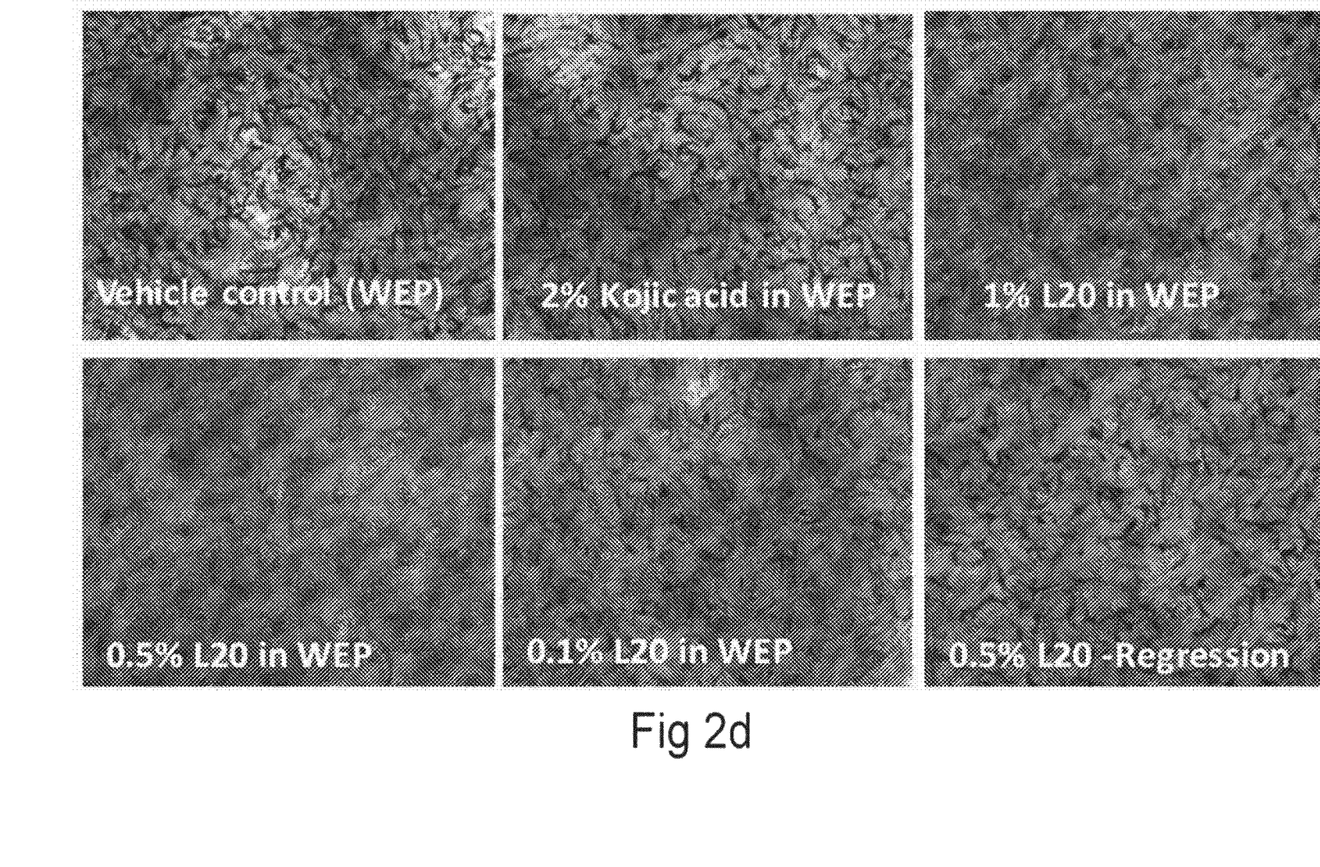

L20 Significantly Inhibits Melanin Synthesis in 3D Skin Equivalent MelanoDerm Models MelanoDerms are co-culture models of keratinocytes and melanocytes and were used to test the ability of L20 as an anti-melanogenic compound. MelanoDerms were derived from a normal adult with darkly pigmented skin. These tissues were treated for two weeks on consecutive days with different doses of L20. One set of cultures were used for regression study, where it was taken off L20 after a week of treatment. Two weeks after treatment, the tissues were tested for melanin content and cell viability (FIG. 2a). Visually, L20 treated melanoderms had significant skin-lightening effect at 0.5% and 1% (FIG. 2b). The melanin content was assayed using a melanin standard curve. Compared to control, L20 alone at 1% decreased melanin content by 60%, and 0.5% by 56% and 0.1% by 44%. A dose dependent decrease in melanin was observed with the different doses of L20 (FIG. 2b-d). Kojic Acid was used as a positive control and decreased melanin by 27%. Additionally, L20 regression was performed in a 0.5% L20 dose group, where removal of L20 resulted in revival of the melanocytes and re-synthesis of melanin (FIG. 2b-d). These studies demonstrate that L20 at 0.5% is non-toxic and significantly decreases melanin. Microscopic observation showed that L20 had decreased melanin at 24 h after the initial treatment. Taken together these studies demonstrate that in MelanoDerm models which have a weak stratum corneum, doses of 0.5% was sufficient to inhibit melanin synthesis and the inhibition is reversible.

L20 Induces Procollagen Synthesis in Human EpiDerm Model and Enhances Anti-Aging Effects Dermal fibroblast plays an important role in photo-aging and skin homeostasis. We determined if L20 had any anti-aging benefit using dermal fibroblasts. Normal human Epi-Derm-FT tissue was used in the study. The Epiderm-FT consists of a fully differentiated epidermal and dermal skin layers. It also has 10-15 layers of stratum corneum and also basal, spinous and granular layers. The tissues were treated with vehicle control and L20 (1%), for 48 h. The tissues were used to measure the expression of procollagen using ELISA assay. The levels of procollagen were normalized to total protein.

Figure 3:
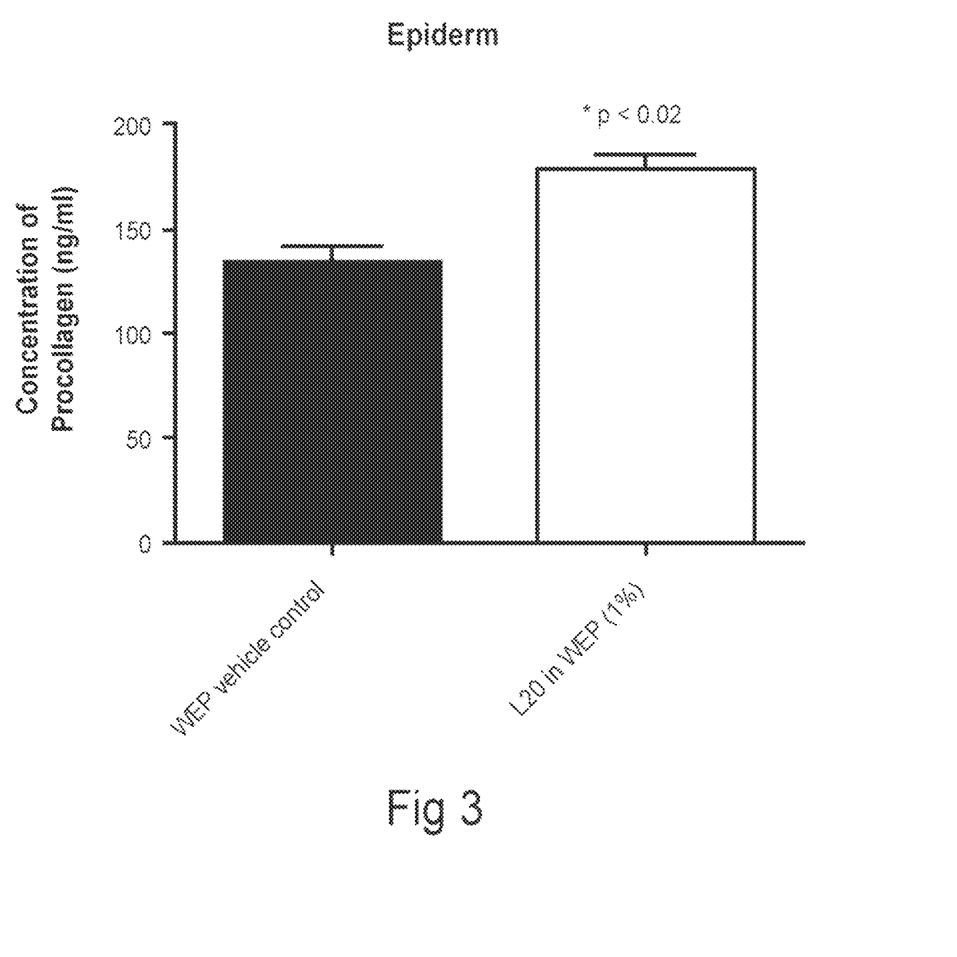
FIG. 3 depicts L20 significantly induces procollagen synthesis of normal Epiderm 3D co-cultures.

L20 was prepared as 1% solution in WEP vehicle consisting of water, ethanol and propylene glycol at native pH. The test material and vehicle (WEP) were applied to a tissue culture model consisting of Reconstructed Human Epidermis (RHE, EpiDermFT™), a highly differentiated 3D tissue model consisting of normal, human-derived epidermal keratinocytes (NHEK) and human dermal fibroblasts cultured on specially prepared tissue culture inserts. Tissues were treated with 25 uL of L20 (1%) or vehicle and maintained for 48 hours. The tissue samples were digested using cell lysis buffer and the expression levels of procollagen protein were determined. Procollagen was quantified using standard ELISA technique (Takara Bio Inc.). As seen in FIG. 3, L20 1% significantly increased procollagen production versus the vehicle control, p<0.02.

Materials and Methods

Cell culture: Normal human epidermal melanocytes (Lonza, Walkersville, Mass.) were grown in special melanocyte media MGM4 with supplements (Lonza, Walkersville, Mass.). Cells were plated and treated with different doses of L20 for 48 h. L20 was initially dissolved in DMSO (100%) and serial dilution were made in media. The stock was diluted a 1000 fold, to have less than 0.001% DMSO in final solution. Microscopic images were taken using 10× magnification. Normal human dermal fibroblasts (Lonza, Walkersville, Mass.) were grown in special fibroblast growth media (Lonza, Walkersville, Mass.). L20 toxicity assay was performed at different doses, and 0.001% and below was found to be non-toxic. To test cell viability, Cell Titer 96® Aqueous One Solution Cell Proliferation Assay was used and absorbance was measured colorimetrically at 490 nm using Tecan microplate reader.

Melanin Reduction assay: Normal human epidermal melanocytes were treated with control or L20 for 7 days, and L20 was replaced on consecutive days. Cells were collected on the $7^{th}$ day and maintained in Solvable (Perkin Elmer, Akron, Ohio) overnight at 65 degrees overnight. In parallel, melanin (Sigma, St. Louis, Mo.) standards were made in Solvable and treated similarly to the samples. Melanin content was then quantified colorimetrically using a Tecan microplate reader at 490 nm.

MelanoDerm Study: MelanoDerms study was performed as per company instructions (Mattek, Ashland, Mass.). MelanoDerm tissues were derived from darkly pigmented skin type. The tissues were stabilized for 24 h and then treated with different doses of L20 (25 ul) in WEP modified vehicle. The MelanoDerms were treated for 2 weeks on consecutive days. Microscopic images were taken every other day. After two weeks, MTT assay was performed using Cell Titer 96® Aqueous One Solution and melanin content was assayed as mentioned in the protocol.

Epiderm Study: Epiderm-FT (Mattek, Ashland, Mass.) was used for the study, derived from neonatal foreskin. The tissues were treated with L20 at 1% (100 ul) and maintained for 48 h. The tissues were shredded using a scissor and treated with cell lysis buffer with protease inhibitors. The cell lysate was analyzed for procollagen using ELISA (Takara, Shiga, Japan) as per instructions and normalized to total protein.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of treating a cosmetic condition or dermatological disorder selected from the group consisting of fine lines, wrinkles, age spots, and for skin lightening comprising topically administering to a subject a composition comprising therapeutically effective amount of a compound selected from the group consisting of: N-Lp-Cys-NH$_2$; N-Lp-Tyr-NH$_2$; N-Lp-Tyr(OAc)-NH$_2$; N-Lp-Pro-NH$_2$; N-Lp-Cys-OEt; N-Lp-Cys-(SAc)-OEt; N-Lp-Cys-(SAc)-NH$_2$; N-Lp-Gly-Cys-NH$_2$; N-Lp-Pro-Cys-NH$_2$; N-Lp-Cys-Gy-NH$_2$; N-Lp-Tyr-Gy-NH$_2$; N-Lp-Gly-Tyr-NH$_2$; N-Lp-Tyr-Cys-NH$_2$; N-Lp-Tyr-Cys-OEt; N-Lp-Gly-Cys-OEt; N-Lp-Gly-Cys-Cys-NH$_2$; N-Lp-Cys-Cys-NH$_2$; N-Lp-Tyr-Cys-Cys-NH$_2$; N-Lp-Gly-Tyr-Cys-NH$_2$; and N-Lp-Pro-Cys-Cys-NH$_2$.

2. The method of claim 1, wherein the compound is selected from the group consisting of: N-Lp-Cys-NH$_2$;

N-Lp-Tyr-NH$_2$; N-Lp-Tyr(OAc)-NH$_2$; N-Lp-Pro-NH$_2$; N-Lp-Cys-OEt; N-Lp-Cys-(SAc)-OEt; and N-Lp-Cys-(SAc)-NH$_2$.

3. The method of claim 1, wherein the compound is a lipoic dipeptide selected from the group consisting of: N-Lp-Gly-Cys-NH$_2$; N-Lp-Pro-Cys-NH$_2$; N-Lp-Cys-Gly-NH$_2$; N-Lp-Tyr-Gly-NH$_2$; N-Lp-Gly-Tyr-NH$_2$; N-Lp-Tyr-Cys-NH$_2$; N-Lp-Tyr-Cys-OEt; and N-Lp-Gly-Cys-OEt.

4. The method of claim 1, wherein the compound is a lipoic tripeptide selected from the group consisting of: N-Lp-Gly-Cys-Cys-NH$_2$; N-Lp-Cys-Cys-Cys-NH$_2$; N-Lp-Tyr-Cys-Cys-NH$_2$; N-Lp-Gly-Tyr-Cys-NH$_2$; and N-Lp-Pro-Cys-Cys-NH$_2$.

* * * * *